(12) United States Patent
Mutke

(10) Patent No.: US 6,505,355 B1
(45) Date of Patent: Jan. 14, 2003

(54) FEMALE URINAL AND METHOD OF USING AND MAKING SAME

(76) Inventor: Hans Guido Mutke, Drygalski-Allee 118/1701, Munich 81477 (DE)

( * ) Notice: Subject to any disclaimer, the term of this patent is extended or adjusted under 35 U.S.C. 154(b) by 0 days.

(21) Appl. No.: 09/831,157

(22) PCT Filed: Nov. 4, 1999

(86) PCT No.: PCT/EP99/08450

§ 371 (c)(1),
(2), (4) Date: Aug. 10, 2001

(87) PCT Pub. No.: WO00/27320

PCT Pub. Date: May 18, 2000

(30) Foreign Application Priority Data

Nov. 6, 1998 (DE) .......................... 198 51 267

(51) Int. Cl.⁷ .............................. A47K 11/00
(52) U.S. Cl. ................... 4/144.3; 4/144.4; 4/144.1
(58) Field of Search ................. 4/144.1–144.4

(56) References Cited

U.S. PATENT DOCUMENTS

| | | | |
|---|---|---|---|
| 3,194,238 A | | 7/1965 | Breece |
| 3,601,125 A | | 8/1971 | Moss |
| 3,964,111 A | * | 6/1976 | Packer .................. 4/144.4 |
| 4,756,029 A | * | 7/1988 | Zieve et al. .............. 4/144.1 |
| 4,815,151 A | | 3/1989 | Ball |
| 4,857,064 A | * | 8/1989 | Mendoza ................. 4/144.2 |
| 5,285,532 A | * | 2/1994 | Sealy .................... 4/144.1 |
| 5,411,495 A | | 5/1995 | Willingham |

FOREIGN PATENT DOCUMENTS

FR 2590160 5/1987

* cited by examiner

*Primary Examiner*—Gregory Huson
*Assistant Examiner*—Tuan Nguyen
(74) *Attorney, Agent, or Firm*—Crowell & Moring LLP

(57) ABSTRACT

A female urinal which makes it possible to urinate at any time and, in particular, while standing. The female urinal includes a curved flexible urine draining and collecting body which covers an area between the legs from approximately above the pubic hair to the perineum and also includes a sealing cushion which is situated on a perimeter thereof. The female urinal is provided with a flexible tube which is located in a lowest area of the urinal and which can be actually fastened to the draining body. The female urinal can be fixed to a belt situated above the iliac crest by way of two bands which are laterally fastened on top and by way of a lower, rear band which is guided from the perineum through the buttocks.

18 Claims, 1 Drawing Sheet

FEMALE URINAL AND METHOD OF USING AND MAKING SAME

This application claims the priority of PCT application PCT/EP99/08450, filed Nov. 4, 1999, the disclosure of which is expressly incorporated by reference herein.

BACKGROUND AND SUMMARY OF THE INVENTION

The invention relates to a female urinal.

A female urinal is known from U.S. Pat. No. 3,194,238 which discloses that, in the event of an involuntary passing of urine, the urine is guided into a container fastened on a user's leg.

In the case of incontinence problems, which may result in an involuntary passing of urine and which often times occurs in women after births and at an advanced age, it is known to use absorptive inserts whose capacity is limited.

It is an object of the invention to provide a female urinal which permits the passing of urine at any time, and particularly when standing.

At least this object is achieved by the female urinal of the present invention. A preferred embodiment of the female urinal comprises a curved flexible urine draining and collecting body capable of being placed against a region of a user's body between the user's legs and extending substantially from above a pubic hair area to a perineum area located between the user's rear vaginal entrance and anus. A sealing cushion is arranged on a perimeter of the draining and collecting body and is capable of contacting the user at least at a portion of the region of the user's body. A hose is arranged on the draining and collecting body at substantially a lowermost area thereof for draining collected urine. A free end of the hose is detachably fastenable on an exterior side of the draining and collecting body. The draining and collecting body is attachable to the user by way of a strap and belt arrangement.

When the hose is folded down, the female urinal is used for the direct spontaneous passing of urine. In other positions of the hose, the female urinal can also be used as a reservoir for a short period of time.

Other objects, advantages and novel features of the present invention will become apparent from the following detailed description of the invention when considered in conjunction with the accompanying drawings.

DETAILED DESCRIPTION OF THE DRAWINGS

Figure 1:
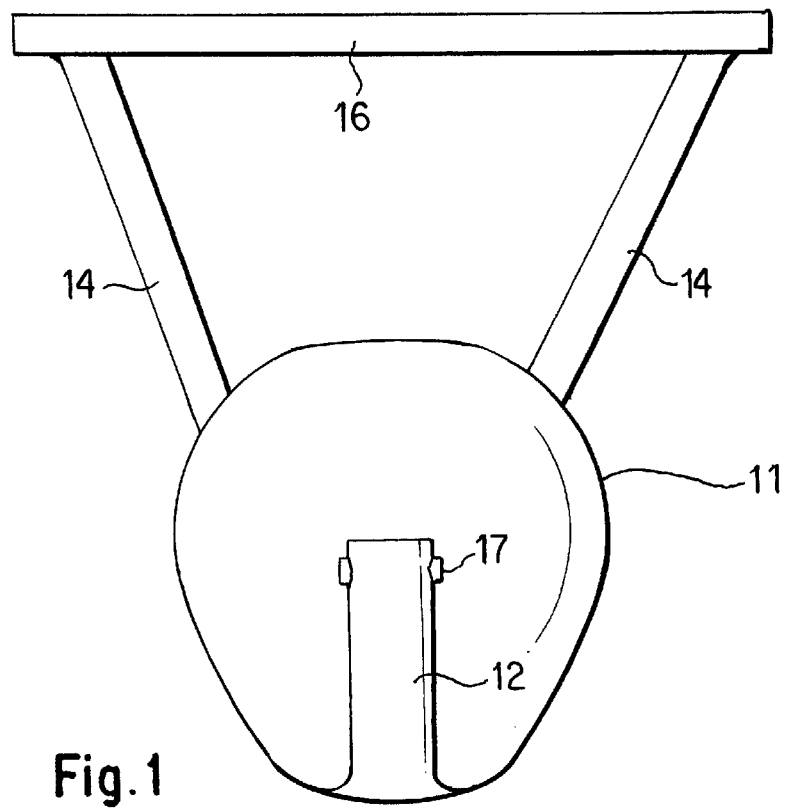
FIG. 1 is a top view of the female urinal.

The female urinal consists of a curved flexible urine collecting and urine draining body 11 which covers the region between a user's legs from approximately above the pubic hair to the perineum between the anus and the rear vaginal entrance and can catch urine in the lower area.

At a perimeter, the draining body 11 is provided with a sealing cushion 18 (shown schematically in FIG. 2) which, in the region of a user's rear vaginal entrance and of the anus comprises a soft material. The draining body 11 has a funnel-shaped opening 13 at a lowest area in which the urine collects, which opening 13 leads into a flexible hose 12. The free end of the hose 12, while being bent, can be sealingly fixed approximately perpendicularly on an exterior side of the draining body 11 by a schematically illustrated clamp or Velcro fastening 17. For draining the urine, the hose is detached from the fixing device 17 and moved into the position illustrated in FIG. 2.

The hose 12 preferably has a length of from 15–20 cm so that it is possible to drain urine without removing a slip being worn by the user by folding down the hose 12.

Figure 3:
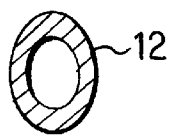
FIG. 3 is a cross-sectional view taken along the line I—I.

A thread can be provided at an end of the hose 12 in order to allow the hose end to be connected optionally by way of an intermediate hose piece to a container which can be fastened on one of the interior sides of the thighs. The cross-section of the hose 12 can expediently be oval, as shown in FIG. 3, so that it does not bulge out and requires therefore, relatively little space.

Figure 2:
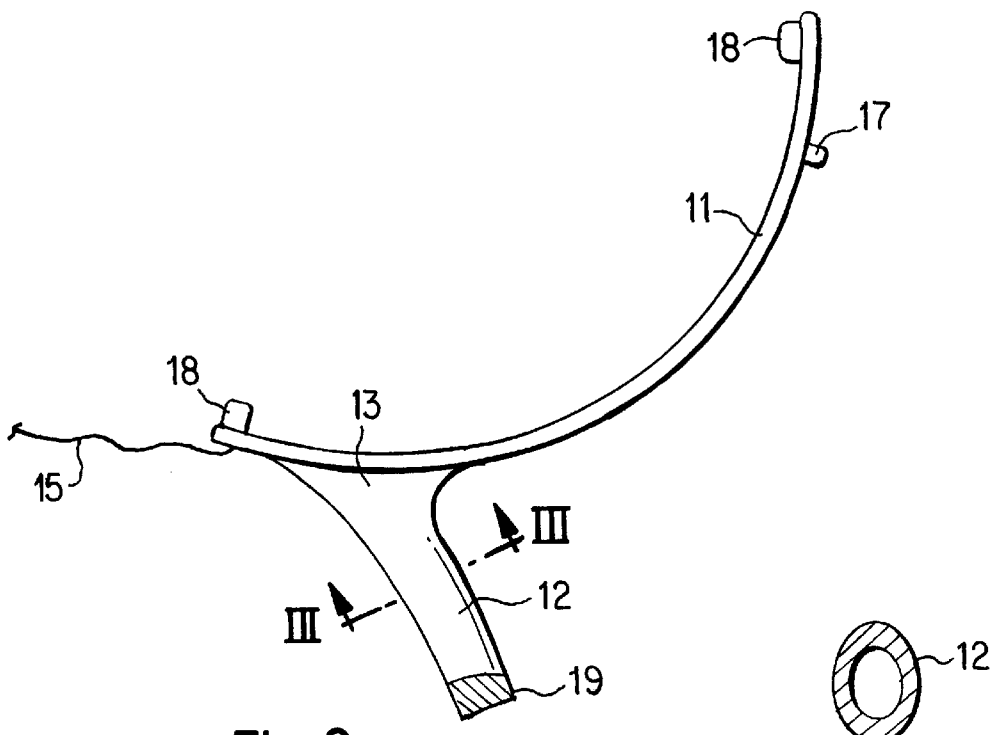
FIG. 2 is a side view thereof.

The fastening of the female urinal takes place by way of two straps 14 which are fastened at the top laterally on the draining body 11 and, when in use, extend in the direction of the user's groins. In addition, a lower rear strap 15, schematically illustrated in FIG. 2, is guided from the perineum through a user's buttocks and can be fixed on a belt 16 above the iliac crest. The lower rear strap 15 is fastened slightly below the circumferential sealing cushion so that, when in use, for a better sealing, the cushion exerts a pressure on the perineum between a user's rear vaginal entrance and anus.

To increase flexibility, the draining body 11 can be constructed to be thinner in an area of the opening 13 leading into the hose 12 than in the remaining portion of the draining body 11.

The female urinal can also be fixedly arranged in a slip so that it can be washed together with the slip. In an upper portion of the draining body 11 a small deodorant package can also be provided.

The female urinal can naturally be manufactured in different sizes and shapes according to any particular requirements.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A female urinal comprising:

a curved flexible urine draining and collecting body capable of being placed against a region of a user's body between the user's legs and extending substantially from above a pubic hair area to a perineum area located between the user's rear vaginal entrance and anus;

a sealing cushion arranged on a perimeter of the draining and collecting body and capable of contacting the user at least at a portion of the region of the user's body; and a hose arranged on the draining and collecting body at substantially a lowermost area thereof for draining collected urine, a free end of the hose being detachably fastenable on an exterior side of the draining and collecting body;

wherein the draining and collecting body is attachable to the user by way of a strap and belt arrangement.

2. A female urinal according to claim 1, wherein the strap and belt arrangement comprises a belt which is worn above an iliac crest of the user, at least one frontal strap which extends in a direction of the user's groin, and one rear strap which is guided from the perineum area through the user's buttocks.

3. A female urinal according to claim 2, wherein the one rear strap is fastened below the sealing cushion such that a pressure is applied to the user's perineum area.

4. A female urinal according to claim 1, wherein the sealing cushion is arranged to contact the user's perineum area and comprises a soft material.

5. A female urinal according to claim 1, wherein an opening of the draining and collecting body connects to the hose and comprises a funnel shape.

6. A female urinal according to claim 5, wherein at least in an area of the opening, the draining and collecting body is relatively thinner than a remaining area of the draining and collecting body.

7. A female urinal according to claim 1, wherein the hose comprises a length of from 15 to 20 cm.

8. A female urinal according to claim 1, wherein a cross-section of the hose is oval.

9. A female urinal according to claim 1, wherein a free end of the hose is provided with a threaded connection.

10. A method of using a female urinal comprising:
providing a female urinal comprising a curved flexible urine draining and collecting body, a sealing cushion arranged on a perimeter of the draining and collecting body, and a hose arranged on the draining and collecting body at substantially a lowermost area thereof for draining collected urine;
placing the draining and collecting body of the female urinal on a body of a user in a region between the user's legs and extending substantially from above a pubic hair area to a perineum area located between the user's rear vaginal entrance and anus; and
attaching the female urinal to the user by way of a strap and belt arrangement.

11. The method of using a female urinal according to claim 10, wherein the strap and belt arrangement comprises a belt which is worn above an iliac crest of the user, at least one frontal strap which extends in a direction of the user's groin, and one rear strap which is guided from the perineum area through the user's buttocks.

12. The method of using a female urinal according to claim 10, wherein a free end of the hose is detachably fastenable on an exterior side of the draining and collecting body.

13. The method of using a female urinal according to claim 10, wherein the sealing cushion is arranged to contact the user's perineum area and comprises a soft material.

14. The method of using a female urinal according to claim 11, wherein the one rear strap is fastened below the sealing cushion such that a pressure is applied to the user's perineum area when attached to the user.

15. A method of making a female urinal comprising:
fabricating a curved flexible urine draining and collecting body capable of being placed against a region of a user's body between the user's legs and extending substantially from above a pubic hair area to a perineum area located between the user's rear vaginal entrance and anus;
connecting a sealing cushion to a perimeter of the draining and collecting body which is capable of contacting the user at least at a portion of the region of the user's body;
connecting a hose to the draining and collecting body at substantially a lowermost area thereof for draining collected urine, the hose being provided such that a free end of the hose is detachably fastenable on an exterior side of the draining and collecting body; and
connecting a strap and belt arrangement to the draining and collecting body such that the female urinal can be attached to the user.

16. The method of making a female urinal according to claim 15, wherein the strap and belt arrangement comprises a belt which is worn above an iliac crest of the user, at least one frontal strap which extends in a direction of the user's groin, and one rear strap which is guided from the perineum area through the user's buttocks.

17. The method of making a female urinal according to claim 16, wherein the one rear strap is fastened below the sealing cushion such that a pressure is applied to the user's perineum area when attached to the user.

18. The method of making a female urinal according to claim 15, wherein the sealing cushion is arranged to contact the user's perineum area when attached to the user and comprises a soft material.

* * * * *